United States Patent [19]

Frigiola

[11] Patent Number: 4,558,714
[45] Date of Patent: Dec. 17, 1985

[54] RESIN INTERFACE DETECTION SYSTEM

[75] Inventor: Frank J. Frigiola, Northvale, N.J.

[73] Assignee: Ecodyne Corporation, Union, N.J.

[21] Appl. No.: 493,827

[22] Filed: May 12, 1983

[51] Int. Cl.[4] .......................... F17D 3/00; F17D 3/01
[52] U.S. Cl. ................................... 137/2; 324/65 R; 324/61 R
[58] Field of Search ............. 73/434, 447, 291, 304 R; 210/96.1, 103, 662; 137/2, 392; 324/65 R, 65 P, 61 P, 61 R

[56] References Cited

U.S. PATENT DOCUMENTS

| | | | |
|---|---|---|---|
| 3,741,683 | 6/1973 | McTamaney | 137/392 |
| 4,061,570 | 12/1977 | Fletcher | 210/96.1 |
| 4,264,439 | 4/1981 | Lefevre | 210/662 |
| 4,265,262 | 5/1981 | Hotine | 137/392 |
| 4,265,263 | 5/1981 | Hobbs | 137/2 |
| 4,298,696 | 11/1981 | Emmett | 210/96.1 |
| 4,323,092 | 4/1982 | Zabel | 210/96.1 |

Primary Examiner—Stanley T. Krawczewicz
Assistant Examiner—Jose M. Solis
Attorney, Agent, or Firm—Dressler, Goldsmith, Shore, Sutker & Milnamow, Ltd.

[57] ABSTRACT

An improved method and system that utilizes conductance values of cationic and anionic exchange resins classified as layers of a mixed resin bed to automatically detect interfaces between the layers is disclosed. The arrangement includes electrical circuitry which initially samples the conductivity of a passing resin slurry. The initial conductivity value is compared to subsequent conductivity values of the passing slurry and the flow of the passing slurry is automatically terminated when the subsequent conductivity value is a certain fraction of the initial conductivity value. Termination in response to this equality condition effectively detects the interface between classified layers of a mixed resin bed.

17 Claims, 2 Drawing Figures

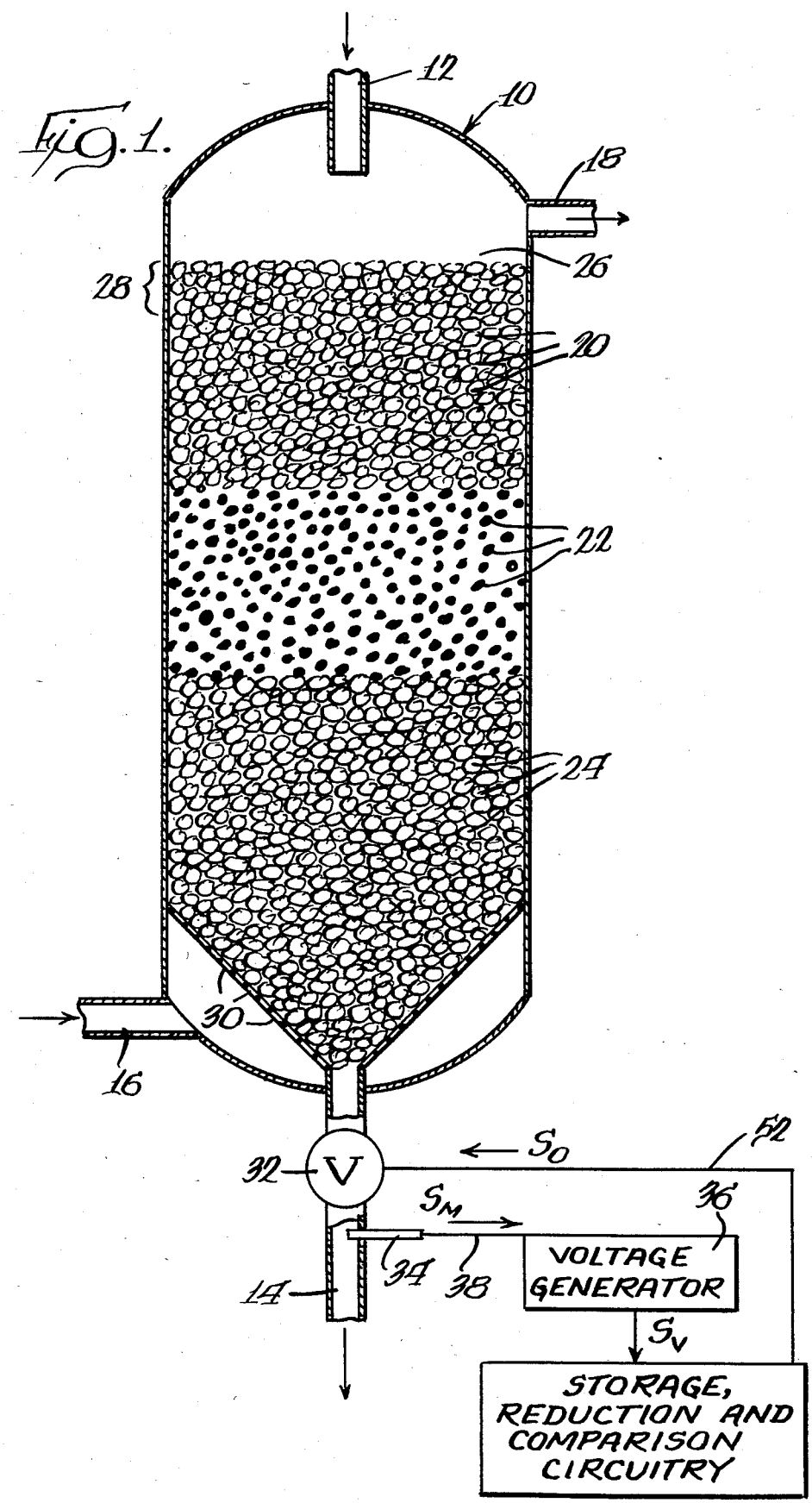

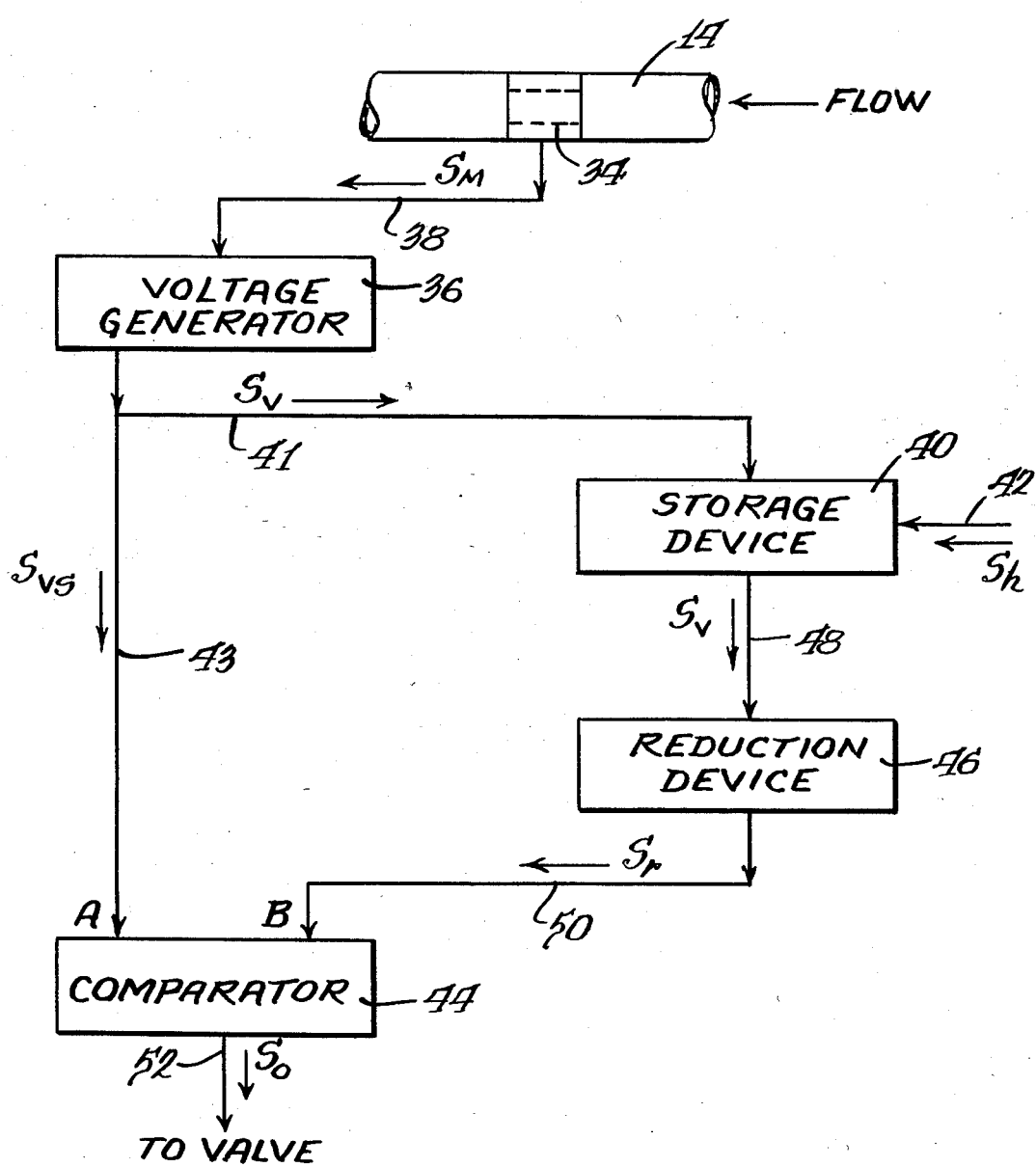

RESIN INTERFACE DETECTION SYSTEM

TECHNICAL FIELD OF THE INVENTION

The present invention relates to the detection of an interface between layers of a classified mixed resin bed, and more particularly to a method and system of detection that utilizes conductance values of cationic and anionic exchange resins classified as layers of a mixed resin bed to detect interfaces therebetween.

BACKGROUND OF THE INVENTION

Beds of mixed cationic exchange and anionic exchange resins are used in many industrial areas. One particular use of such resin beds is in deionization of water used in generating steam, wherein the water used should be substantially free from dissolved ionic materials so that a build-up of those previously dissolved salts may be avoided in the boiler and associated parts. Thus, water going into the boiler is first passed through the mixed resin bed to exchange cations and anions for protons and hydroxide ions, respectively.

A mixed resin bed has a finite exchange lifetime that is related to the exchange capacities of the resin, the amount of water passing through the bed and the ionic content of the water. After the exchange capacity of the resin bed is exhausted, the resin must either be regenerated or discarded.

An exhausted mixed resin bed is rarely discarded due to the relatively high cost of the resins. Rather, the exhausted mixed resin bed is regenerated to provide cation and anion exchange resins having substantially their original exchange capacity.

Several methods have been used to regenerate the exhausted resins in the bed. Typically, the resins are separate. Then, the exhausted cation exchange resin is treated with a protic acid so that protons replace the exchanged cations present in the exhausted resin, while the exhausted anion exchange resin is treated with a solution containing hydroxide ions to replace the anions. A method useful for carrying out the regeneration of exhausted resins is disclosed in co-pending, co-assigned U.S. patent application Ser. No. 493,828 filed concurrently herewith and now abandoned.

One general method for separating the cation exhange resin from the anion exchange resin utilizes resins having different densities, and suspends those resins in a classifying fluid such that they classify into layers in accordance with their differing densities. A problem with this technique has been that the densities of the different resins are not substantially different enough to afford a substantially complete separation of one resin from the other. To alleviate this problem, a quantity of substantially inert, particulate material having a density intermediate between that of the cation exchange resin and the anion exchange resin has been used.

Problems still exist in the separation of the resins even when an inert material having an intermediate density between that of the two exchange resins is used. These problems are associated with the determination of the location of the interface between the inert material and the cationic exchange resin, which is usually the heaviest, as well as the interface between the inert material and the anion exchange resin, which is usually the least dense.

Two methods of detecting the interface between the exchange resin and the inert material based on the conductivity properties of slurries of the material in a classifying fluid are those of U.S. Pat. Nos. 4,264,493 and 4,298,696. However, neither method is completely successful in automated systems.

In U.S. Pat. No. 4,264,439, a conductivity sensor is used to continuously measure the conductivity of a classified resin slurry as it passes from a holding tank. The sensor is connected to a recorder which exhibits a distinct change in the conductivity of the slurry to indicate the interface. The valve permitting passage of the slurry out of the holding tank is closed to retain the anion exchange resin within the holding tank when the distinct change is recorded.

There is, however, no discussion in U.S. Pat. No. 4,264,439 of what change the patentee relies upon, other than a drop, for determining the locations of the interface between the exchange resin and the inert material. An operator apparently must be taught the type of change to look for, be required to watch the recorder, detect that the required change in the conductance value has occurred and then subsequently shut the valve stopping passage of the slurry.

In U.S. Pat. No. 4,298,696, a conductivity sensor is used to determine the transition between the resins by detecting a decrease in the conductivity of the slurry as it passes out of its holding tank. A decrease to a set conductance value is implied for one embodiment, thereby making the use of classifying waters having substantially different conductance values identifying the interface between separations difficult. An alternative embodiment for use with classifying waters having variable conductivity utilizes two conductivity sensors at separate points to detect a predetermined difference in the conductivity. Again, however, there is no teaching of how to use the data gathered from such a sensor. There is also no teaching stating that the change in measured conductance can be used to automatically stop the flow of the resin slurry.

Each of the above methods therefore either requires the presence of an operator to make the detection of the change in conductivity which occurs when the interface between the exchange resin and inert material passes the sensor, or the use of the classifying fluid which itself has a relatively constant conductivity so that the preset value of conductance can be used by a machine or an operator for selecting the position of the interface.

It would therefore be beneficial if neither an operator nor a classifying fluid of relatively constant conductivity need be used for selecting the location of the interface between the exchange resin and inert material. The presently described invention provides such a benefit.

SUMMARY OF THE INVENTION

The present invention provides a method for deleting a resin layer interface and a system for carrying out the method of detecting the interface between the layers of resins of an exhausted, classified mixed resin bed. Further, the presently disclosed method and apparatus carries out the teachings of co-pending and co-assigned U.S. patent application Ser. No. 493,828, filed concurrently herewith, which provides a method for separating and regenerating the resins of an exhausted, classified mixed resin bed.

The mixed resin bed is classified with a classifying fluid in a container to form a substantially vertical column of slurry having a top end and a bottom end. The exhausted cation exchange resin, particulate inert material and exhausted anion exchange resin, are classified in the slurry substantially so that the cation resin forms the bottom layer, the inert material forms the intermediate layer, and the anion exchange resin forms the top layer.

The slurry is passed out of the container from an area near the bottom end of the column while the classification is maintained. The detection system of the present invention provides a conductivity measuring device to measure the conductivity of the passing slurry and to generate an initial voltage signal. After a time delay, allowing the conductance value to become substantially constant, the initial voltage signal is stored in a device for storing such signals determining an initial conductance value. Upon storage of the initial voltage signal, the initial signal is processed by a device for generating a reduced voltage signal proportional to the initial voltage signal. Such a device generates a voltage signal that is approximately at most about thirty percent of the initial voltage signal representing the initial conductance value. The system also provides for measuring subsequent conductance values of the passing slurry which generates subsequent voltage signals.

Each of the subsequent voltage signals representing the subsequent conductance values of the passing slurry are compared to the reduced voltage signal in a device for comparing voltage signals. When one of the subsequent voltage signals is equal to the reduced voltage signal an output is generated from the comparing device which closes a valve and terminates the passage of surry out of the container. Upon such termination, the slurry that passes out of the container contains substantially all of the exhausted cation exchange resin which is preferably collected.

The present invention has several benefits and advantages. One such benefit is that the interface detection system herein illustrated is not dependent upon a supply of classifying fluid having a particular, predetermined conductivity such as is required with the previously used devices.

Another benefit of the detection system of the present invention is that the location of the interface between the exchange resin and inert material can be determined without the assistance of a human operator. In addition, a human operator is not necessary to adjust the detection system when separation of exchange resins is carried out for resin slurries suspended in classifying fluids of varying conductances.

Another of the advantages of this invention is that it is also not dependent upon the initial conductivity of the cation exchange resin, nor on the conductance value of the classifying fluid.

Numerous other advantages and features of the present invention will become readily apparent from the foregoing detailed description of the invention, from examples, from the claims, and from the accompanying drawings.

BRIEF DESCRIPTION OF THE DRAWINGS

FIG. 1 shows a cross-sectional view of a schematic representation of a classified mixed bed along with its pertinent apparatus; and FIG. 2 is a detailed electrical circuit diagram of the interface detection system showing the relevant circuit elements in block diagram form.

DESCRIPTION OF THE PREFERRED EMBODIMENT

A method and a corresponding system for detecting an interface in accordance with the present invention is disclosed hereinbelow in conjunction with FIG. 1. FIG. 1 shows a schematic cross-section of a container or vessel 10 having a resin inlet tube 12 located near the top of the vessel 10 and a resin outlet pipe 14 located near the bottom of the vessel. A classifying fluid inlet pipe 16 is also located near the bottom of the vessel 10, while a classifying fluid outlet pipe 18 is located near the top of the vessel.

The vessel 10 includes an exhausted mixed bed resin which includes an anion exchange resin 20, a particulate inert material 22 and a cation exchange resin 24. The exchange resins and the inert material are classified within the vessel 10 with a classifying fluid 26, which is preferably water, to form a substantially vertical column of slurry having a top end 28 and a bottom end 30. The resins and inert material are classified such that the exhausted cation resin 24 forms a bottom layer, the exhausted anion exchange resin 20 forms a top layer and the inert material 22 forms a layer intermediate between the anion and cation exchange resin layers.

The resin outlet pipe 14 includes a valve 32 for permitting the passage of the slurry of classified, exhausted resin in classifying fluid out of the vessel 10. In order to effectuate the method and system of detecting interface between the classified layers, the present invention includes a conductivity sensor 34 for sensing the conductivity of the passing slurry. Such a conductivity sensor 34 can be embodied in several forms. The form contemplated in the illustrated embodiment includes, but is not limited to, an in-line conductivity cell, such as Kennicott Water Treatment Company, Model 2110-380.

As can be seen in FIG. 1, the conductivity sensor 34 is located within resin outlet pipe 14 below valve 32. The vessel 10 contains the classified layers of exchange resin which are arranged from bottom to top such that the cation exchange resin 24 is at the bottom, inert material 22 is in the middle and anion exchange resin 20 is at the top. Upon need for emptying the contents of the vessel 10, valve 32 located in the resin outlet pipe 14 is opened to permit the passage of the classifying slurry of resin and inert material and allows the slurry to descend and exist from the vessel 10. As the passing slurry flows by the conductivity sensor 34, the sensor measures the conductivity of the passing slurry and generates a measuring signal $S_m$ representing the conductance value of the slurry.

As can be appreciated by those skilled in the art, the conductivity sensor 34 can take many forms, and may incorporate separate measuring and qenerating devices for sampling the conductance of the slurry and thereby generating a measuring signal $S_m$ in response to the conductivity measurement. It is further noted, that the conductance value as used herein can be measured in many forms. As used herein, "conductance value" may mean conductance measured in units of volts, mohs, amperes, ohms or other such machine readable units. Therefore, such measuring and signal generating components of the conductivity sensor 34, may be separate elements or integrated as necessary to perform the desired function of sampling the conductivity value of the passing slurry.

Conductivity sensor 34 is operably connected to a voltage generator 36 by cable 38 or by a similar signal transmitting path. The type of voltage generator contemplated in the illustrated embodiment includes, but is not limited to, a conductivity monitor such as Leeds and Northrup Model 70751021120201206. The generator 36 translates the measuring signal $S_m$, transmitted from the conductivity sensor 34, into a voltage signal $S_v$ representing the conductance value of the passing slurry.

In order to obtain an accurate initial conductance value of the flowing cation exchange resin 24 that will be emptied from the vessel 10 upon opening of valve 32, it is necessary to delay the use of the initial sampled conductance value of the passing slurry. Such a delay allows the flow of the slurry to become constant thereby avoiding any erroneous readings that may be generated at the beginning of the slurry flow.

As can be seen in FIG. 2, the voltage signal being transmitted from the voltage generator 36 at any qiven moment is transmitted to two destinations. The first destination is to a storage device 40 via a cable 41. The storage device 40 allows for retention of the voltage signal therein, in response to an input hold signal $S_h$ transmitted along the cable 42 or a similar signal transmitting path. This type of delayed sampling circuitry provides the necessary time delay between the initial flow of slurry from the vessel 10 and the time the initial conductance value of the passing cation slurry is stored for use. The type of storage device contemplated in the illustrated embodiment includes, but is not limited to, a sample track and hold module such as Rochester Instrument Systems Model XSC 136048572 A/B/C/-D/E/F/H/J-I.

Once the input hold signal $S_h$ is activated to allow retention of the initial conductance value within the storage device 40, the storage device 40 will no longer accept subsequent voltage signals from the voltage generator 36. However, the second destination of the signal generated by the voltage generator 36 will accept such subsequent voltage signal $S_{vs}$. These subsequent voltage signals $S_{vs}$ are transmitted along cable 43 to a comparator 44. The type of comparator contemplated in the illustrated embodiment includes, but is not limited to, a special deviation equalizer alarm module, such as Rochester Instrument Systems Model XET 1228-82008. Such a comparator device functions to produce an output signal in response to two input siqnals being of equal value. Modification of the off-the-shelf deviation equalizer alarm module will allow the user to obtain such an output. However, other such comparators are available that will produce an output in response to two input values that are equal, making the need for such modification unnecessary.

The subsequent voltage signals $S_{vs}$ are received at input A of the comparator 44 continuously, and change in response to the conductivity of the slurry passing through the valve 32 and by conductivity sensor 34. Therefore, as cation exchange resin 24 is removed from vessel 10, conductivity values are continuously being sensed and after the cation exchange resin 24 is totally removed from the vessel 10, inert material 22 will begin to drain from the vessel 10. At such time, the conductivity value sensed by conductivity sensor 34 will drop substantially from the sensed conductivity value of the passing cation exchange resin 24. Preferably the conductivity valve will drop to a value that is approximately at most thirty percent of the initial conductance value which is represented by the initial voltage signal stored in the storage device 40. This decreased conductivity value of the inert material 22 will be received by the comparator 44 at input A in the form of the subsequent voltage signals $S_{vs}$.

As further can be seen from FIG. 2, the storage device 40 is operably connected to a reduction device 46 by cable 48. Such a reduction device is commercially available and includes, but is not limited to, a ratio bias transmitter, Model SC 1398, sold by Rochester Instrument Systems. This reduction device 46, accepts the stored voltage signal representing the initial conductance value from the storage device 40 and generates a reduced voltage signal that represents at most thirty percent of the initial stored voltage signal representing the initial conductance value of the passing slurry. More preferably, the reduction device generates an output that is at most twenty-five percent of the initial voltage signal $S_v$ representing the initial conductance value.

This reduced voltage signal $S_r$ is also transmitted to the comparator 44 at input B by cable 50. Unlike input A, received from the voltage generator 36, input B remains fixed at this reduced value of the initial stored voltage signal. Therefore, as the changing input A is reduced it will eventually reach a reduced value equal to the value of input B, and comparator 44 will generate an output signal $S_o$ in response to this condition. Such equality will occur as the concentration of the passing slurry decreases due to the depletion of the cationic exchange resin 24 from the vessel 10.

As the cation exchange resin 24 is removed from the vessel 10, inert material 22 will begin to enter the resin outlet pipe 14 and reduce the conductivity of the passing slurry and thereby reduce the conductivity value sensed by conductivity sensor 34. As the subsequently sensed value reduces, the value will be reached where input A of comparator 44 will be equal to input B. At this time the conductivity value of the passing slurry which is proportional to voltage signal at input A of the comparator will be equal to the reduced signal value which is preferably at most twenty-five percent of the initial conductivity value of the passing slurry present at input B. When this condition is satisfied, the comparator 44 will generate an output signal $S_o$ which will be transmitted to terminate the resin transfer step by cable 52. Upon reception of the output signal, all valves will close stopping the flow of resin from the vessel 10. Once such a condition is reached and input A is equal to input B, the comparator is locked into an equality mode and remains in such a mode until it is reset.

Termination of the passage of the slurry at the above conductance value separates the exhausted cation exchange resin 24 from the inert material 22 and the exhausted anion exchange resin 20 which remain in vessel 10. Therefore, the detection system of the present invention effectively detects the interface between the cation exchange resin 24 and the inert material 22. Such separation allows the cation exchange resin 24 to be regenerated by mixing it with a solution that would be different from the regeneration solution used for an anion exchange resin. A method useful for regeneration of cation and anion exchange resins, as well as a method for initially classifying such resins, is disclosed in coassigned U.S. patent application Ser. No. 493,828, filed concurrently herewith and now abandoned.

In reference to FIG. 2, the input hold signal $S_{hd}$ is delayed in order to allow the conductivity of the passing cation exchange resin slurry to become constant. In the illustrated example this is facilitated by providing at most a three-minute delay before the input hold signal $S_h$ is qenerated. After generation of the input hold signal $S_o$ the storage device 40 retains the initial conductance value which remains in the storage device until such time as the input hold signal $S_h$ changes state. This assures that the initial conductance value stored is held in the storage device 40 throughout one cycle of the emptying of vessel 10 and that the initial conductance value held is the value that is representative of the true conductance value of the passing cation slurry.

It should also be noted that the storage device 40 may contain several elements facilitating such sampling, storing, and acceptance of an input hold signal $S_h$. Such circuitry includes, but is not limited to, a sample track and hold integrated circuit, as noted hereinbefore. Further, the circuitry described in the illustrated embodiment typically operates on voltage signals that are within the value range of one to five volts D.C. This type of voltaqe signal range is common among commercially available circuit elements such as the elements described previously herein.

The circuitry herein described comprising the interface detection system of the present invention need not be separate components, but may be within one apparatus. Similarly, the function of translating sensed conductivity into measured conductance values need not be carried out in one device, but may be carried out in a plurality of devices, as may the functions of storing and comparing conductance values.

The present invention has been described qenerally with respect to a preferred embodiment. It will be clear to those skilled in the art that modifications and/or variations of the disclosed method can be made without departing from the scope of the invention as set forth. This invention is defined by the claims that follow.

what is claimed is:

1. A method of detecting the interface between classified layers of a mixed resin bed in a slurry passing from an area near the bottom of a container having cation and anion exchange resins classified substantially so that cation exchange resin forms the bottom layer, inert material forms an intermediate layer and anion exchange resin forms the top layer, comprising the steps of:
    (a) measuring the conductivity of said passing slurry;
    (b) generating a measuring signal representing the conductance value of said passing slurry;
    (c) generating an initial voltage signal representing the conductance value of said passing slurry responsive to the measuring signal representing an initial conductance value of said passing slurry;
    (d) storing said initial voltage signal representing the initial conductance value of said passing slurry in a means for storing electrical signals;
    (e) generating a reduced voltage signal representing at most 30 percent of the initial voltage siqnal representing the initial conductance value of said passing slurry;
    (f) measuring subsequent values of the conductivity of said passing slurry;
    (g) generating subsequent measuring signals representing subsequent conductance values of said passing slurry;
    (h) generating a voltage signal representing each of said subsequent conductance values of said passing slurry responsive to each of said subsequent measuring signals;
    (i) comparing each of the subsequent voltage signals with the reduced voltage signal proportional to said stored voltage signal representing the initial conductance value in a means for comparing voltage signals;
    (j) generating an output from said comparing means when one of the subsequent voltage signals is equal to the reduced voltage signal; and
    (k) terminating the flow of said passing slurry automatically in response to the output generated by said comparing means.

2. The method according to claim 1, wherein said measurement of said conductivity of said passing slurry is effected by a conductivity sensing element.

3. The method according to claim 2, wherein said measurement of said conductivity of said passing slurry and said generating of said measuring signal is effected by a conductivity cell monitoring the conductivity of said passing slurry.

4. The method according to claim 1, wherein said storing of the initial voltage signal, representing the initial conductance value of said passing slurry, takes place after said initial voltage signal has become substantially constant in response to initiation of a hold signal received by a means for storage of electrical signals.

5. The method according to claim 4, wherein said initiation of said hold signal takes place automatically after approximately at most a three minute delay from the instant the first measurement of conductivity of said passing slurry is taken, and said initial voltage value remains stored in said means for storage after initiation of said hold signal until such time as said hold signal changes state.

6. A system for detecting the interface between classified layers of a mixed resin bed in a slurry passing from an area near the bottom of a container having cation and anion exchange resins classified substantially so that cation exchange resin forms a bottom layer, inert material forms an intermediate layer and anion exchange resin forms a top layer, comprising:
    (a) means for measuring the conductivity of said passing slurry;
    (b) means for generating a measuring signal representing the conductance value of said passing slurry;
    (c) means for generating an initial voltage signal in response to and proportional to the measuring signal representing an initial conductance value of said passing slurry;
    (d) means for storing said initial voltage signal representing the initial conductance value of said passing slurry;
    (e) means for generating a reduced voltage signal representing at most 30 percent of the initial voltage signal representing the initial conductance value of said passing slurry;
    (f) means for measuring subsequent values of conductivity of said passing slurry;
    (g) means for generating subsequent measuring signals representing subsequent conductance values of said passing slurry;
    (h) means for generating a voltage signal representing each of said subsequent conductance values of said passing slurry responsive to each of said subsequent measuring signals;
    (i) means for comparing each of the subsequent voltaqe signals with the reduced voltage signal proportional to said stored voltage signal representing the initial conductance value; and (j) means for generating an output from said comparing means when one of the subsequent voltage signals is equal to the reduced voltage signal.

7. The interface detection system of claim 6, wherein said measuring means and measuring signal generating means includes a conductivity sensing element.

8. The interface detection system of claim 6, wherein said storing means stores the initial voltage signal representing the initial conductance value of said passing slurry in response to initiation of the hold signal received by said storing means.

9. The interface detection system of claim 8, wherein said initiation of said hold signal takes place automatically after approximately at most a three minute delay from the instant the first measurement of conductivity of said passing slurry is taken, and said initial voltage value remains stored after initation of said hold signal until such time as said hold signal changes state.

10. A system for detecting the interface between classified layers of a mixed resin bed in a slurry passing from an area near the bottom of a container having cation and anion exchange resins classified substantially so that cation exchange resin forms a bottom layer, inert material forms an intermediate layer and anion exchange resin forms a top layer, comprising:
  (a) means for in-line measuring of the conductivity of said passing slurry;
  (b) means for generating a measuring signal representing the conductance value of said passing slurry;
  (c) means for generating and transmitting an initial voltage signal representing the conductance value of said passing slurry in response to and proportional to the measuring signal representing an initial conductance value of said passing slurry;
  (d) means for sampling and holding said initial voltage signal representing the initial conductance value of said passing slurry;
  (e) means for generating and transmitting a reduced voltage signal representing at most about 25 percent of the initial voltage signal representing the initial conductance value of said passing slurry;
  (f) means for in-line measuring of subsequent values of the conductivity of said passing slurry;
  (g) means for generating subsequent measuring signals representing subsequent conductance values of said passing slurry;
  (h) means for generating and transmitting a voltage signal representing each of the subsequent conductance values of said passing slurry responsive to each of said subsequent measuring signals;
  (i) means for comparing each of said subsequent voltage signals representing said subsequent conductance values with the reduced voltage signal proportional to said stored voltage signal representing the initial conductance value of said passing slurry;
  (j) means for generating an output from said comparing means when one of the subsequent voltage signals is equal to the reduced voltage signal; and
  (k) means for automatically terminating the flow of said passing slurry in response to the output generated by said comparing means.

11. The interface detection system of claim 10, wherein said in-line measuring means and said measuring signal generating means includes an in line conductivity sensing cell.

12. The inerface system of claim 10, wherein said means for generating and transmitting an initial voltage signal includes a conductivity transmitter.

13. The interface detection system of claim 10, wherein said means for sampling and holding said initial voltage signal includes sample, track and hold circuitry.

14. The interface detection system of claim 10, wherein said means for generating and transmitting a reduced voltage signal includes a bias transmitter.

15. The interface detection system of claim 10, wherein said storing means stores the initial voltage signal representing the initial conductance value of said passing slurry after said initial voltage has become substantially constant in response to initiation of a hold signal received by said storing means.

16. The interface detection system of claim 15, wherein said initiation of said hold signal takes place automatically after approximately at most a three minute delay from the instant the first measurement of conductivity of said passing slurry is taken, and said initial voltage valve remains stored in said means for storage after initiation of said hold siqnal until such time as said hold signal changes state.

17. The interface detection system of claim 10, wherein said voltage signals are within the value range of 1 to 5 volts D.C.

* * * * *